(12) United States Patent
Robson et al.

(10) Patent No.: US 6,491,920 B1
(45) Date of Patent: *Dec. 10, 2002

(54) POLYPEPTIDES AND DNA ENCODING SAME

(75) Inventors: Kathryn Jane Hallowes Robson, Oxford (GB); Jennifer Ruth Sadler Hall, Swindon (GB)

(73) Assignee: Imperial College Innovations Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/317,114

(22) Filed: May 24, 1999

Related U.S. Application Data

(63) Continuation of application No. 08/867,414, filed on Jun. 2, 1997, now abandoned, which is a continuation of application No. 08/454,619, filed on May 31, 1995, now Pat. No. 5,811,106, which is a continuation of application No. 08/266,802, filed on Jun. 27, 1994, now abandoned, which is a continuation of application No. 07/655,390, filed as application No. PCT/GB89/00895 on Aug. 4, 1989, now abandoned.

(30) Foreign Application Priority Data

Aug. 12, 1988 (GB) ............................................. 8819209

(51) Int. Cl.⁷ .................... A61K 39/015; A61K 31/711; C12N 15/86; C12N 15/866
(52) U.S. Cl. ................................ 424/185.1; 424/184.1; 424/191.1; 424/265.1; 424/268.1; 424/269.1; 424/272.1; 514/2; 514/44; 536/23.1; 536/23.7; 536/24.1; 435/320.1; 435/455; 435/456; 435/325; 435/348; 435/69.1; 435/91.4; 435/91.41; 435/91.42
(58) Field of Search .............................. 435/320.1, 455, 435/456, 325, 348, 69.1, 91.4, 91.41, 91.42; 536/23.1, 23.7, 24.1; 514/44, 2; 424/184.1, 185.1, 191.1, 265.1, 268.1, 269.1, 272.1

(56) References Cited

PUBLICATIONS

John M. Walker et al, Techiniques In Molecular Biology, 1983.*

* cited by examiner

Primary Examiner—David Guzo

(57) ABSTRACT

Proteins from the merozoite stage of the malaria parasite, fragments and derivatives thereof, DNA coding for the said proteins, and processes for the preparation of the proteins and plasmid and viral vectors useful in said processes. The invention also provides antibodies to the proteins and immunological compositions containing the proteins.

51 Claims, 3 Drawing Sheets

Figure 1:
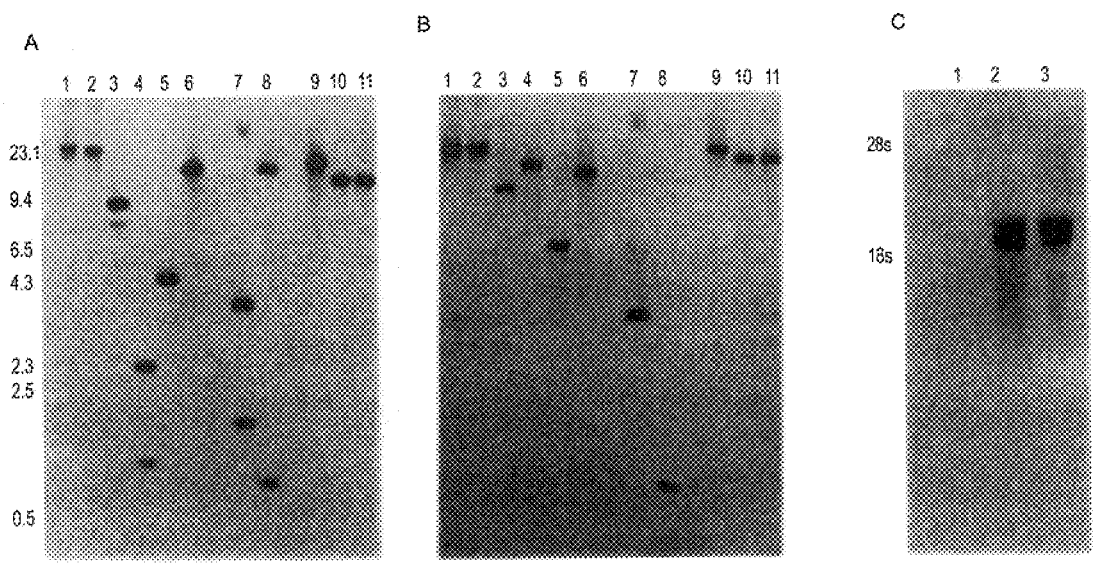

☐ TRAP coding sequence
▨ Baculovirus DNA flanking the polyhedrin gene
▨ pUC sequence
■ Polyhedrin gene promoter

POLYPEPTIDES AND DNA ENCODING SAME

This is a continuation of application Ser. No. 08/867,414, filed Jun. 2, 1997, now abandoned; which is a continuation of application Ser. No. 08/454,619, filed May 31, 1995, now U.S. Pat. No. 5,811,106; which is a continuation of application Ser. No. 08/266,802, filed Jun. 27, 1994, now abandoned; which is a continuation of application Ser. No. 07/655,390, filed Feb. 12, 1991, now abandoned; which is a national stage of application Ser. No. PCT/GB89/00895, filed Aug. 4, 1989.

This invention relates to polypeptides, and to DNA encoding same, produced by human malaria parasites. It also relates to methods of preparing the polypeptides, to antibodies thereto and compositions for use against malaria.

Plasmodium falciparum malaria is one of the most common infectious diseases in the world today, threatening up to 40% of the world's population. It is a disease of the Third World. There are between 150 and 300 million cases of this disease annually, over 1% of cases are fatal, babies and young children being the most vulnerable. With the advent of insecticides and new parasiticidal drugs developed after World War II it was felt that the disease could be eradicated. The early attempts proved very successful but with time the parasite has developed resistance to drugs such as chloroquine and the mosquito vector (Anopheles) has developed resistance to DDT. As a consequence of this it is necessary to develop new approaches to try to combat the disease. As immunity to the disease develops with increasing age, in endemic areas, a vaccine, together with new anti-malarials and insecticides need to be developed if the disease is to be eradicated.

Current research programmes, throughout the world, are involved in defining what antigens might form part of a useful vaccine. The complex life-cycle of the parasite means that a simple vaccine based on one antigen may not be adequate and that an effective vaccine will probably require antigens from different development stages.

The human malaria parasite, Plasmodium falciparum, has a complex life-cycle, during which different antigens are produced at particular developmental stages. The major antigen on the sporozoite surface is the circumsporozoite or CS protein, which probably determines the specificity of the interaction between the parasite and liver cells. CS protein contains two conserved amino acid sequences, known as regions I and II, which are separated by a repeating amino acid motif.

The cloning of the gene for this protein has permitted the development of various vaccines. To date vaccine trials using parts of the CS protein have proved disappointing. Immunity to sporozoites does not necessarily prevent the erythrocytic phase of the life-cycle which is associated with clinical disease. Only one sporozoite needs to evade the immune system for clinical disease to occur. Currently CS protein is the only well-characterised protein known to be involved in host-cell recognition. The merozoite is the developmental stage capable of re-infecting fresh red cells. Antibodies which prevent gametocyte differentiation within the mosquito are useful in breaking the transmission cycle as well. Another complexity is the antigenic variation displayed by the parasite. A vaccine against the asexual erythrocytic parasite, need only be partially effective to reduce the severity of the disease. A vaccine against the asexual blood stages of P. falciparum has been developed by Patarroyo et al (Nature Vol. 332, 1988, p158) based on the use of synthetic peptides, but this has not proved to be totally effective.

We have now found that polypeptides sharing certain sequence motifs with CS protein are produced during the erythrocytic or merozoite stage of the parasite life-cycle.

Accordingly, the present invention provides a polypeptide from the group comprising:

a) a polypeptide having the amino acid sequence of Formula I;

b) polypeptides having substantially the same structure and biological activity as a);

c) fragments, derivatives and mutants of a) or b) significantly involved in their biological activity;

d) oligomeric forms of a), b) or c) significantly involved in their biological activity.

It will be understood by those skilled in the art that some variation in structure may occur in naturally occurring biologically active polypeptides and that malarial proteins in particular display antigenic variability. Provided that structural variations do not eliminate the biological activity of interest such as, for example, involvement in parasite recognition of red cells, red cell attachment or merozoite invasion, the present invention includes such variations within its scope.

Thus, although formula I relates to a cloned isolate of P. falciparum from Thailand known as T.9/96, the scope of the invention also includes, for example, a polypeptide derived from another Thailand isolate known as K1. This was known to differ from T9/96 in lacking a Hinf 1 restriction site and having an extra Bgl II site, which has been confirmed by sequencing. Polypeptide from K1 differs from T9/96 in certain details as set out in Table 1 but the conserved regions are intact.

Both T9/96 and K1 are obtainable from the WHO Registry of Standard Strains of Malaria Parasite, Dept. of Genetics, University of Edinburgh, United Kingdom.

TABLE 1

Comparison of DNA and Polypeptide from T9/96 and K1

| Amino acid residue | Nucleotide Position in codon | T9/96 | K1 | Amino Acid T9/96 | K1 |
|---|---|---|---|---|---|
| 39 | 1 | A | C | S | R |
| 46 | 1 | C | G | Q | E |
| 83 | 3 | T | A | D | E |
| 90 | 1 | G | C | V | L |
| 92 | 1 | G | A | V | I |
| 98 | 2 | A | G | K | R |
| 119 | 2 | G | A | R | K |
| 134 | 2 | C | G | T | S |
| 179 | 2 | G | A | S | N |
| 277 | 1 | A | T | I | L |
| 290 | 1 | T | C | W | R |
| 297 | 1 | G | C | D | H |
| 311 | 2 | C | T | S | F |
| 312 | 1 | T | G | S | A |
| 314 | 1 | C | G | Q | E |
| 337 | 2 | A | G | D | G |
| 341 | 3 | C | A | N | K |
| 359 | 1 | G | C | E | Q |
| 361 | 1 | A | G | K | E |
| 398 | 2 | A | T | H | L |
| 412 | 1, 2 | AA | TC | N | S |
| 490 | 2 | A | G | E | G |

Generally, about 5% variation in amino acid residues may be tolerated but, as will be understood by those skilled in the art, some regions of the molecule and some residues are more significant than others. Conserved regions which play an important role in biological activity are likely to be less tolerant of variation (e.g. in and around the region displayed for TRAP in Formula III), whereas antigenically important regions, for example around the RGD sequence (residues 307–309 of Formula I) are more subject to variability. TRAP as used herein is an abbreviation for "Thrombospondin related anonymous protein" and indicates one or more of the polypeptides of the present invention. Other regions may be somewhat less significant but there is some evidence of biological activity associated with NP or PN sequences. By "conserved" we mean having significant homology of amino acid residue sequences with other proteins of interest. Thus, for example, the region from about residue 244 to about residue 291 has significant homology with CS proteins from various strains of malaria parasite and with thombospondin and properdin framework proteins as illustrated in Formula III. It is not possible to put precise numerical limits on the degree of homology but 80% or greater say, would in many examples be expected to be significant.

The present invention also provides fragments of the above polypeptides, preferably containing a conserved sequence, for example, a fragment from the region extending from amino acid residues 244 to 291 of Formula I and more particularly a polypeptide selected from the following group;

a) WDEWSPCSVTCGKGTRSRKR
b) WDEWSPCSVTCGKGTR
c) EWSPCSVTCGKG
d) PCSVTCGKG
e) WSPCSVTCG

The single letters in the formula represent the following naturally occurring L-amino acids: (A) alanine, (C) cysteine, (D) aspartic acid, (E) glutamic acid, (F) phenylalanine, (G) glycine, (H) histidine, (I) isoleucine, (K) lysine, (L) leucine, (M) methionine, (N) asparagine, (P) proline, (Q) glutamine, (R) arginine, (S) serine, (T) threonine, (V) valine, (W) tryptophan, (Y) tyrosine.

Derivatives of the polypeptide of the invention are, for example, where functional groups, such as amino, hydroxyl, mercapto or carboxyl groups, are derivatised, e.g. glycosylated, acylated, amidated or esterified, respectively. In glycosylated derivatives an oligosaccharide is usually linked to asparagine, serine, threonine and/or lysine. Acylated derivatives are especially acylated by a naturally occurring organic or inorganic acid, e.g. acetic acid, phosphoric acid or sulphuric acid, which usually takes place at the N-terminal amino group, or at hydroxy groups, especially of tyrosine or serine, respectively. Esters are those of naturally occurring alcohols, e.g. methanol or ethanol.

Further derivatives are salts, especially pharmaceutically acceptable salts, for example metal salts, such as alkali metal and alkaline earth metal salts, e.g. sodium, potassium, magnesium, calcium or zinc salts, or ammonium salts formed with ammonia or a suitable organic amine, such as a lower alkylamine, e.g. triethylamine, hydroxy-lower alkylamine, e.g. 2-hydroxyethylamine, and the like.

Mutants of the polypeptides of the invention are characterised in the exchange of one (point mutant) or more, about up to 10, of its amino acids against one or more of another amino acid. They are the consequence of the corresponding mutations at the DNA level leading to different codons.

The present invention also includes within its scope oligomeric forms of the said polypeptides, e.g. dimers and trimers. Such forms may occur naturally and be significant to biological activity. Within the term "oligomeric form" we wish to include both covalently linked molecules and molecules linked by weaker intermolecular bonding, such as hydrogen bonding, into conformationally significant forms.

The present invention also provides DNA sequences coding for the polypeptides of the invention. The DNA sequence coding for the T9/96 strain of $P.$ $falciparum$ is displayed in Formula I but the scope of the present invention extends to variations not affecting the amino acids encoded and also variations such as found in nature and encoding for the K1 strain referred to above, for example.

DNA according to the present invention may be recovered from malaria parasite DNA and genomic libraries by methods known in the art and it will be understood that once the sequence is known direct amplification is possible, by the polymerase chain reaction, for example. (Saiki et al, Science 1985 Vol. 230 pp1350–1354)

The polypeptides of the invention may be prepared by chemical synthesis, where the number of amino acid residues is not too large, or by expression of the appropriate DNA sequences in a host/vector expression system.

Recombinant vectors comprising the appropriate DNA, together with other functional sequences, such as promoter and marker genes, may be made by methods known in the art.

Suitable vectors include recominant plasmids comprising a DNA sequence of the present invention cloned into pUC13 (Pharmacia) or pAc YM1, (Inst. of Virology, Mansfield Road, Oxford, England).

Recombinant viral vectors may be obtained by incorporating the appropriate DNA sequence into viral DNA by methods known in the art. (See, for example, DNA Cloning, Volume II, D. M. Glover, published 1985, IRL Press, Oxford, England.) One suitable method, according to the present invention, involves the combination of a plasmid with a virus using a co-transfection process in a suitable host cell.

Using the plasmid hereinafter identified as pKKJ17, for example, together with the $Autographa$ $californica$ Nucleopolyhedrosis Virus (AcNPV) in $Soodoptera$ $frugiperda$ cells, recombinant virus containing DNA sequence of the present invention may be reproducibly isolated, for example that hereinafter identified as vKKJ17.

According to a further aspect of the present invention we provide antibodies to the polypeptides of the invention. The antibodies may be made by techniques known in the art (see for example: Antibodies, A Laboratory Manual, E. Harlow and D. Lane, Cold Spring Harbour 1988).

The polypeptides of the invention are likely to be useful in the preparation of vaccines and the like against malaria. For this purpose they may be incorporated as active ingredients in suitable carriers, adjuvants, etc. possibly in combination with other immunologically active materials to provide protection against different stages of the malaria parasite.

Technical and theoretical aspects of the invention will now be discussed for purposes of clarification but it should be understood that the utility of the invention does not depend upon the precise accuracy of this theoretical analysis.

The polypeptides of the invention share certain sequence motifs common to other well-characterised proteins. The most significant homology is based around the sequence WSPCSVTCG, three copies of which have been identified in region I of thrombospondin (TSP), six copies in properdin (P), and one copy in all the circumsporozoite proteins sequenced so far. In addition it shares with certain extracellular glycoproteins, including TSP, the cell-recognition signal (RGD), which has been shown to be crucial in the interaction of several extracellular glycoproteins with the members of the integrin superfamily. Because of their relationship with thrombospondin, the polypeptides of the invention are referred to herein as thrombospondin related anonymous proteins or TRAP proteins. Unlike the CS protein, TRAP proteins are expressed during the erythrocytic stage of the parasite life-cycle.

To search for CS protein-related sequences in the genome of *Plasmodium falciparum*, an oligonucleotide probe having the sequence ACC.ATT.TCC.ACA.GGT.TAC.ACT.A-CA.TGG (shown in Formula IIA), corresponding to region II, was used to probe a genomic Southern blot of *Plasmodium falciparum* (T9/96) DNA. T9/96 is a cloned isolate of *P. falciparum* from Thailand, obtainable from The Dept. of Genetics, Institute of Animal Genetics, Kings Buildings, West Mains Road, Edinburgh, UK. The predicted 9kb Eco RI and 800 bp Bst N 1 fragments were detected. The same probe was used to screen two genomic *Plasmodium falciparum* DNA libraries, one a complete Eco RI digest cloned in lambda-gt 11 and the other a partial Eco RI digest cloned in lambda-gt 10. The true CS protein sequence was not expected to be found in either of these libraries because the two vectors have an upper limit of 8 kb. Several clones were isolated, all of which shared a 2.35 kb Eco RI fragment. The DNA from this fragment as well as that of a neighbouring Eco RI fragment was sequenced (shown in Formula I). The sequence detected by the oligonucleotide, together with the probe sequence, is shown in Formula IIA. There is an open reading frame (Formula I), starting with a methionine residue, which is 559 amino acids long and encodes a protein Mr 63,300. The amino acid sequence includes the conserved nonapeptide Trp-Ser-Pro-Cys-Ser-Val-Thr-Cys-Gly, explaining why the oligonucleotide probe detected this new gene (Formula IIB). This sequence and variations on it are found in TSP, CS protein and properdin. Formulae III illustrate the conserved sequence homology between the TRAP protein of Formula I and CS protein sequences from *Plasmodium falciparum* (P.f.), *P. vivax* (P.v.), *P. knowlesi* (P.k.), *P. cynomolgi* London strain (P.c.), *P. berghei* (P.b.), *P. yoelii* (P.y.), TSP, and the properdin framework. Sequence alignment was achieved using the ALIGN program [Dayhoff et. al., Meth. Enzymol. 91, 524–545, (1983)]. The single letter amino acid code has been used and residues in common with TRAP have been boxed.

The protein sequence of TRAP has two hydrophobic domains at either end of the molecule. The first, at the amino terminal end is probably a signal sequence; the second, at the carboxy terminus, resembles a transmembrane sequence. There is a cluster of cysteine residues around and including the conserved amino acid sequence suggestive of a secondary structure formed from intermolecular or intramolecular disulphide bonds. Cysteine residues occur in similar positions around the conserved regions in CS protein, TSP and properdin. Evidence for such secondary structure is provided by the fact that antibodies raised against the CS derived peptide containing region II gave poor reaction to both native and denatured CS protein, suggesting a highly ordered configuration [Ballou et. al., Science 228, 996–999, (1985)]. Beyond the conserved region the sequence becomes rich in praline but this does not form part of a repeat characteristic of many other malaria proteins. Submerged within this sequence is an RGD motif (amino acids 307–309), which is characteristic of many glycoproteins involved in cell recognition. TRAP is the first malarial protein to have this motif. TSP has such an RGD motif as well as an IQQ motif which has been implicated in cross-linking to Factor $XIII_a$; TRAP also has an IQQ motif (amino acids 76–78). There are four possible sites for N-glycosylalion. Like most malarial antigens, the amino acid composition is unusual in that it is particularly rich in asparagine and proline.

The CS protein gene is only expressed during the sporozoite stage of the life-cycle of the malaria parasite. A different protein (CRA or Ag 5.1), expressed in asexual parasites, bears an epitope which is cross-reactive with monoclonal antibodies directed against the NANP repeat structure in CS protein. Sequence data for this protein reveals an area of homology to $(NANP)_2$ and no other sequence characteristic of the CS protein.

Northern blot analysis using a CS gene probe did not detect any RNA species from erythrocytic stages. Similar analysis (see FIG. 1C) using a TRAP gene (of Formula I) probe showed that RNA species of about 20S were detected in the two isolates examined, ITO and FCR3A2, indicating that the TRAP gene is expressed during the erythrocytic stage of the life-cycle but not in EBV-transformed lymphocytes, indicating that the TRAP probe was not detecting human sequences present in blood due to contamination and is therefore parasite-specific. The size of the RNA transcript is compatible with it coding for a protein of Mr 63,300. Antibodies have been raised to TRAP beta-galactosidase fusion proteins. They react on Western blots with a protein of about 65 kd (the predicted size for the TRAP gene product) as well as a number of other parasite proteins including mature infected erythrocyte surface antigen (MESA) and 332. Further examination of the deduced amino acid sequence for TRAP reveals several motifs centred around a Glu-Glu (E-E) motif, and this probably explains this cross-reaction. Indirect immunofluorescence suggests that TRAP is synthesized during the final stages of schizogony.

The occurrence in two both vertebrate and invertebrate stages of *Plasmodium falciparum* of a highly conserved motif which is also present in thrombospondin and in properdin suggests that TRAP proteins might be of functional significance. A possible role for the CS protein of sporozoites is recognition and entry into hepatocytes. Synthetic peptides from regions I bind specifically to hepatocytes in vitro; such studies have not yet been reported for region II. Two other parasite-cell interactions are critical in the life cycle of *Plasmodium falciparum*. Its virulence is related to its propensity to sequester in deep vascular beds. This process, which depends on the interaction of parasite-induced modifications on the red cell surface with receptors on endothelial cells involves thrombospondin. Both thrombospondin itself and thrombospondin antibodies inhibit the cytoadherence of infected red blood cells in in vitro models of sequestration. This, taken together with the evidence that implicates platelet glycoprotein IV (the thrombospondin receptor) as having a crucial role in cytoadherence would be consistent with the presence on the infected erythrocyte of a parasite-induced thrombospondin analogue. The cytoadherence antigen Pf EMP I is thought to be 300 kd; this does not exclude TRAP as there is some evidence that cytoadherence involves parasite modification of a host protein and TRAP could fulfill this role.

The other parasite-cell interaction is the recognition and invasion of red cells by free merozoites. If TRAP were to be present on the free a merozoite surface the homology with properdin, which binds to C3b, might play a role in the recognition of C3b or its breakdown products on the red cell surface. The closely related parasite *Babesia rhodiani* has developed a strategy for entering erythrocytes involving C3b. The observation that entry of red cells by *Plasmodium*

*falciparum* merozoites does not require serum complement components does not exclude the involvement of complement components already on the red blood cell surface.

BRIEF DESCRIPTIONS OF FORMULAE AND DRAWINGS

Figure 2:
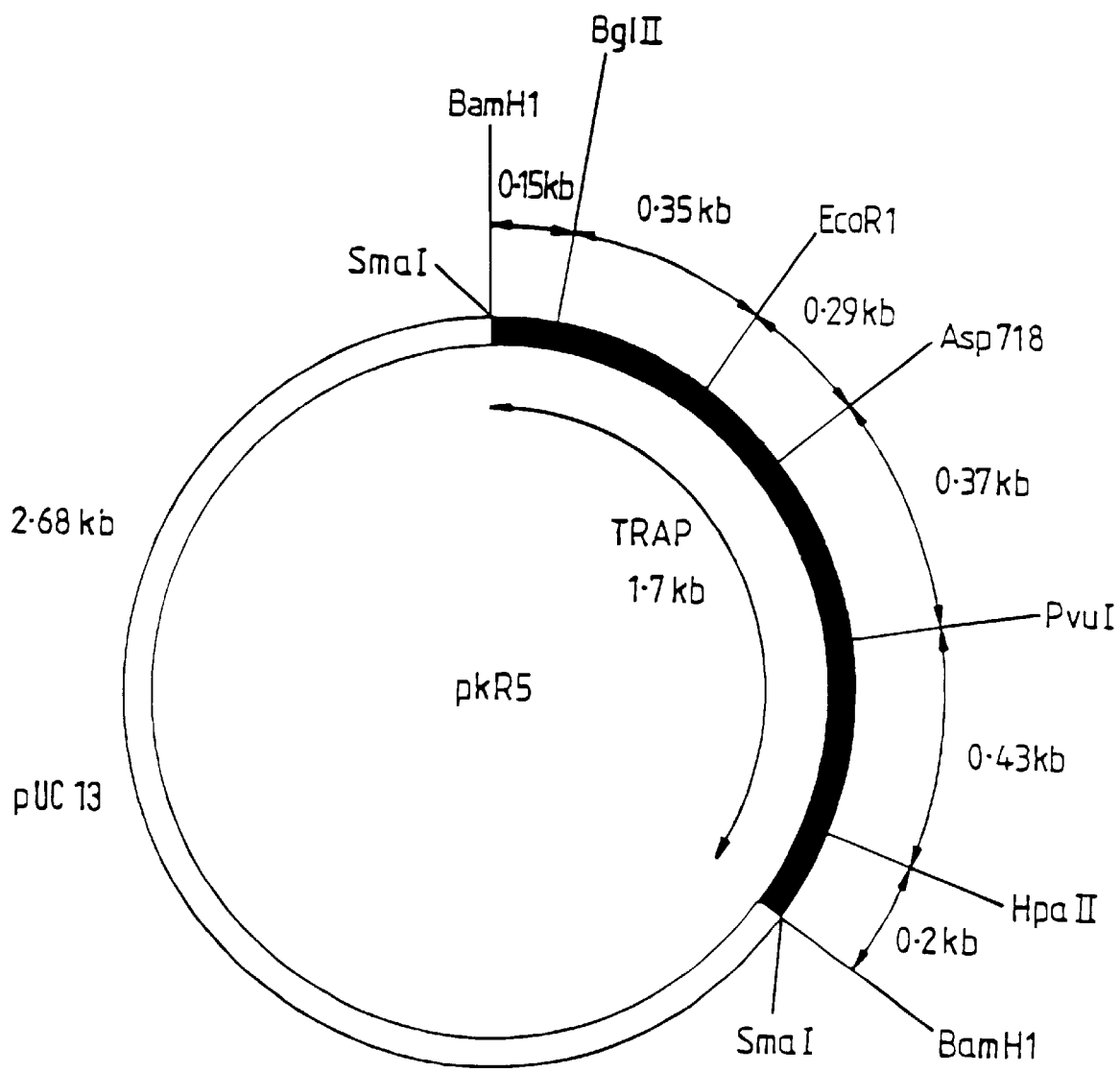

Examples of the invention and other technical details will now be described with reference to the accompanying formulae and drawings in which:

Examples of the invention and other technical details will now be described with reference to the accompanying formulae and drawings in which:

| | |
|---|---|
| Formula I | represents the amino acid residue sequence of a polypeptide according to the present invention, using the single letter amino acid code, and the nucleotide sequence of a DNA coding therefore, together with flanking non-coding sequences. Nucleotides are numbered from 1 to 3102 and amino acid residues from 1 to 559 corresponding to coding nucleotides from 312 to 1989; |
| Formula IIA | shows a comparison of a 27-base oligonucleotide probe and a DNA sequence detected by it from a lambda gt11 genomic library of *P. falciparum* and |
| Formula IIB | is a comparison of amino acid and nucleotide sequences complementary to the probe sequences; |
| Formulae III | show a comparison of amino-acid sequences around and including the conserved nonapeptide motif of the polypeptide of Formula I with other proteins; |
| FIG. 1A | represents a Southern blot analysis of DNA from a cloned line T9/96 of *P. falciparum* hybridised with the polypeptide of FIG. 1, used as a probe; |
| FIG. 1B | is similar to FIG. 4A but hybridised with a CS protein probe; |
| FIG. 1C | represents a Northern blot analysis of total RNA from EBV transformed lymphocytes and from two *P. falciparum* isolates; |
| FIGS. 2 and 3 | are diagramatic representations of plasmids pKR5 and pKKJ17 respectively as provided by the invention showing restriction sites and other features. |

Referring to Formulae IIA and IIB, one 27-base oligonucleotide sequence was synthesized from the amino acid sequence PCSVTCGNG in region II of CS protein. The complementary strand was synthesized so that both DNA and RNA sequences could be detected. The oligonucleotide was synthesized on an Applied Biosystems model 308A (Trade Mark) synthesizer by monomer addition of phosphoramidites to a solid support. The de-protected probe was purified by preparative polyacrylamide gel electrophoresis. The end-labelled oligonucleotide was used to screen $4 \times 10^5$ plaques (on *E.coli* Y1088) of an *Eco* RI digest of *P. falciparum* T9/96 DNA cloned into the *Eco* RI site of lambda-gt11. Six positive plaques were identified which rescreened. These contained 2.35 kb *Eco* RI fragments. Hybridisation was carried out for 16 hours at 37° C. in 6xNET (1xNET=0.15 M NaCl, 0.015 N tris-HCl pH 8.0, 1 mM EDTA), 5xDenhardt's, 0.5% NP40, 100 micrograms/ml sheared salmon sperm DNA. Washing was done at 37° C. in 6xSSC (1xSSC=0.15 M NaCl, 0.015 M sodium citrate) 0.1% SDS, followed by a one minute wash in the same solution at 60° C. The filters were subjected to autoradiography for 16 hours with pre-flashed X-ray film.

The 2.35 kb *Eco* RI insert from the lambda-gt11 phage was subcloned into pUC8 and M13mp10. Dideoxy sequencing of this fragment revealed an incomplete open reading frame. A second library was constructed by cloning a partial *Eco* RI digest of T9/96 into lambda-gt10, and was screened with the original 2.35 kb fragment. $1.1 \times 10^5$ plaques (on *E. coli* NM514) were screened and clones with overlapping sequences were obtained. The complete DNA sequence of the TRAP gene and its flanking sequences were established using the chain termination procedure of Sanger et. al. [J.Mol. Biol., 143, 161–178 (1980)]. The information was obtained from 'shotgun' clones in M13mp10 which enabled both strands to be sequences. Gaps were filled in using custom-synthesized oligonucleotide primers. This approach proved the most efficient way of deriving the DNA sequence where there was an absence of restriction enzyme sites; a particular problem in regions of A-T rich DNA. The DNA sequence handling programmers of Staden were used to analyze the data [Nucl. Acids Res. 10, 4731–4751 (1982)]. The site to which the oligo-nucleotide probe hybridised is underlined in Formula I. The asparagine residues which are potential sites for N-linked glycosylation have asterisks. The RGD sequence (residues 307–309) is overlined. The IQQ motif (residues 76–78) is boxed.

Referring to FIGS. 1A and 1B, (Southern blots) lanes 1–11 correspond to restriction digests with the following enzymes, Asp 718, Bam HI, Bgl II, *Eco*RI, Hinc II, Hind III, Tag I, Bst NI, Hha I, Hpa II and Msp I respectively.

In FIG. 1C, (Northern blots) lane 1 corresponds to EBV transformed lymphocytes (25 µg); lane 2, *P. falciparum* isolate ITO (Brazilian strain) (25 µg) and lane 3 *P. falciparum* FCR3 A2 (Rockerfeller strain) (cloned) (25 µg).

Southern blotting and hybridisation was carried out as described by Woo et al. [Nature 306, 151–155 (1984)]. Northern blotting was as described by Robson et al. [Proc. Natl. Acad. Sci. USA, 79, 4701–4705 (1982)]. Hybond-N (Trade Mark) membranes were used to permit re-hybridisation of the same filter. The filter in panel A was initially hybridised with the two *Eco* RI fragments corresponding to the TRAP sequence; the signal was removed and the filter rehybridised with that containing the CS protein gene sequence. The probe in panel C was the same as in panel A. The filter in panel C was also hybridised to the same probe as panel B: no hybridization signal was observed.

In order to produce larger quantities of the polypeptides and DNA of the invention, in purer form the following procedures were followed.

Polycolonal antibodies to several purified beta-galactosidase TRAP fusion proteins were generated. Purification of the proteins involved denaturation by detergent and poly acrylamide gel electrophoresis so that any important conformational epitopes were destroyed. As these antibodies also recognized other parasite antigens on Western blots they could not be used to purify native TRAP from cultured parasites. It was therefore decided to pursue an alternative strategy using eukaryotic expression vectors designed to produce large quantities of native protein which should be correctly processed and easily purified.

One possible expression system utilizes baculoviruses. The baculovirus expression system allows high level expression of foreign genes in a eukaryotic environment. It takes advantage of natural gene regulation, that is the very late but highly abundant expression of the polyhedrin gene. Owing to the large size of baculovirus genomes, most recombinant virus construction relies on in vivo recombination to replace a viral allele with the gene of interest. Transplacement plasmids contain the site for foreign gene insertion as well as flanking viral sequences that provide homologous sequences for recombination. Co-transfection of cells with viral and recombinant plasmid DNAs allows cell-mediated allelic replacement of the target viral gene with the plasmid-borne foreign gene construct.

For foreign genes to be expressed abundantly in the baculovirus expression system they need to be engineered to lack introns as well as the majority of 5' and 3' flanking sequences. TRAP genes do not contain introns and using the polymerase chain reaction (PCR) we have engineered the TRAP gene of FIG. 1 with a complete open reading frame as a Bam HI restriction fragment and cloned into the transfer vector pAcYMl (obtainable from the Institute of Virology, Oxford, England).

Figure 3:
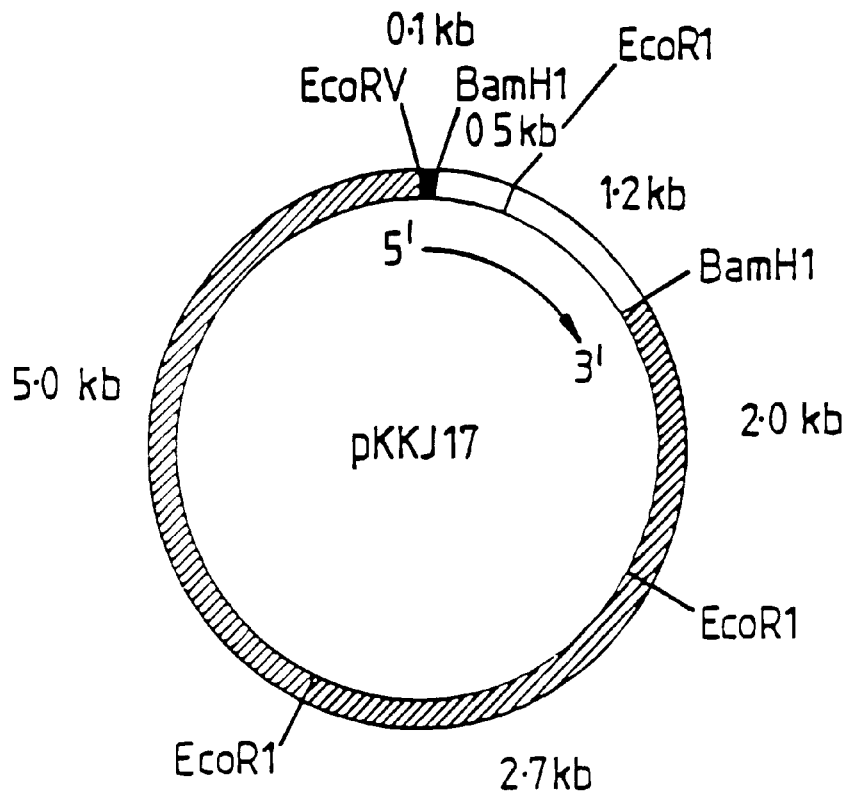

This is carried out as follows. Two oligonucleotide primers were designed containing Bam HI sites as well as the 5' and 3' ends of the TRAP genes. The sequences of these two primers are:

A GGATCCAAAATAATGAATCATCTTGGG
B GGATCCGTATTATATTTAATTCCACTCG the underlined sequences correspond to the ends of the coding sequence. In primer A this is the coding strand and in primer B this is the complementary strand; this is necessary because DNA is always synthesized in the 5' to 3' direction. The DNA amplified was a genomic subclone of T9/96 DNA in M13. The reaction was set up as described by Saiki et al (Science, 1985, Vol. 230, pp1350–1354) utilizing Taq 1 polymerase [(1 mM) oligonucleotide primers A and B, 10 mM deoxynucleoside triphosphates and 1 ng of RV9 (the subclone of TRAP in M13)]. The cycle times and temperatures were 1' at 93° C., 1'37° C., 5' at 72° C., the number of cycles was 15. After amplification the complete reaction mix was extracted with phenol/CHCl$_3$, chloroform, followed by gel filtration to remove the unused deoxynucleoside triphosphates. The ends of the DNA product were repaired using the Klenow fragment of deoxyribonuclease 1 and fresh deoxynucleoside triphosphates. The reaction was again terminated by phenol/CHCl$_3$ extraction and gel filtration using Sephadex G50/80. The 5' ends of the DNA were phosphorylated using T4 polynucleotide kinase and adenosine triphosphate. The reaction was terminated by phenol/CHCl$_3$ extraction and the DNA recovered by propan-2-ol precipitation. This material was used as the substrate of a ligation reaction using T4 DNA ligase and phosphatased Sma 1 cut pUC13 (Pharmacia). Constructs containing the desired insert were obtained and their authenticity checked by DNA sequencing. One such plasmid was pKR5. The fragment could be released from pUC13 by Bam H1 digestion demonstrating that the necessary restriction sites would permit transfer of the transplacement plasmid pAcYMl. pKR5 was digested with Bam HI and Hae III, the reaction terminated by phenol/CHCl$_3$ extraction, followed by ethanol precipitation. This digest was carried out to prevent gel purification of the desired 1.7 kb Bam HI fragment prior to religation into the Bam HI site of pAcYMI. A similar ligation and transformation was carried out with the insert and the new vector pAcYMI. Again constructs containing the desired fragment were obtained. The orientation of the insert containing the TRAP sequence relative to the polyhedrin promoter was checked by restriction mapping and sequencing. This construct has been called pKKJ17 and the map is shown in FIG. 3. A deposit of this plasmid has been made at the National Collections of Industrial and Marine Bacteria Ltd. (NCIMB), Torrey Research Station, P.O. Box 31, 135 Abbey Road, Aberdeen, AB9 8DG, United Kingdom on Jul. 14th, 1989 under Accession Number NCIMB 40,164.

Using pKKJ17, we were able to set up a transfection of Spodoptera frugiperda cells as outlined below. 25 µg of pKKJ17 together with 1 µg of caesium chloride purified *Autographa californica* Nucleopolyhedrosis Virus (AcNPV) DNA was prepared in Hepes buffered saline pH 7.5 containing 10 mM glucose and 125 mM CaCl$_2$. A calcium/DNA complex was allowed to form over a 45 minutes period prior to addition to freshly plated *Spodoptera frugiperda* cells (1.5×10$^6$ cells) and incubation for 1 hr at room temperature. The DNA precipitate was removed and fresh medium (TC100) added and the cells incubated at 20° C. until a cytopathic effect had been observed (3 days post transfection). The viruses produced by these cells were both wild type AcNPV and recombinant AcNPV containing the TRAP gene. Plaque purification following titration permitted the isolation of pure recombinant virus. This was facilitated by the fact that wild type AcNPV had intact polyhedrin gene and so produced occluded plaques whereas recombinants did not. The differences between the two types of plaque can be visualized using light microscopy.

After the first transfection one recombinant plaque was seen and purified. Approximately one in two hundred plaques were recombinant provided that caesium chloride purified viral DNA was used in earlier stages. Recombinant virus was identified as vKKJ17 and a deposit has been made on Jul., 14th 1989 at European Collection of Animal Cell Cultures (ECACC), Public Health Service Laboratory, Centre for Applied Microbiology and Research, Porton Down, Salisbury, Wiltshire, SP4 OJG, United Kingdom, under Accession number 89071402.

AcNPV is the prototype virus of the family Baculoviridae. During infection of *Spodoptera frugiperda* cells with this virus two types of virus progeny are produced, extracellular virus particles and occluded virus particles. The occluded virus particles are embedded in proteinaceous material, comprising the polyhedrin protein. Under the microscope these are visible as polyhedra. These viral inclusions are an important part of the life cycle as it is through ingestion of these particles that insect larvae become infected.

The recombinant virus vKXJ17 lacks the polyhedrin gene and so cannot make occluded particles. The polyhedrin gene has been replaced by the TRAP gene. As a onsequence the virus vKKJ17 remains infectious for the tissue culture system (*Sp. frugiperda*) but cannot infect insect larvae. The expression of the TRAP protein is under the control of the polyhedrin protein. This means that TRAP protein starts to be synthesized 20 hr post infection. The polyhedrin protein is the most adundant protein in the wild-type virus and generally foreign genes under the expression of the polyhedrin promoter produce high levels of the protein of interest. In vKKJ17 the TRAP sequence is on a Bam H1 fragment which replaces all of the polyhedrin coding sequence.

Baculoviruses are double stranded DNA viruses, where the DNA is circular. The size of the DNA is 135 kb.

Production of TRAP was tested by infecting *Sp. frugiperda* cells with recombinant virus vKKJ17 and growing the cells for 72 hrs before SDS-polyacrylamide gel electrophoresis and Western blotting. The antibody used in the detection system was rabbit polyclonal produced using the beta-galactosidase fusion material. This recombinant virus did in fact synthesize TRAP polypeptide according to the present invention. Further analysis demonstrated that this material was secreted into the culture supernatant. This factor aided purification.

At high multiplicity of infection there is no requirement to maintain *Sp. frugiperda* cells in medium containing serum. Advantage was taken of this fact so cells were infected at high multiplicity of infection with vKKJ17 and incubated at 28° C. in the absence of serum for 72 hrs. The infected cells were removed by centrifugation (Beckman JA10 4K, 10'4° C.).

The clarified supernatant containing TRAP and virus particles was concentrated by $(NH_4)_2SO_4$ precipitation followed by dialysis. The virus particles were removed by centrifugation (Beckman JA20, 20K, 4° C., 90'). This material was subjected to ion exchange chromatography (Mono Q, Pharmacia, LKB). Fractions containing TRAP were concentrated by lyophilisation prior to further purification by gel filtration (TSK G3000, Pharmacia, LKB). TRAP was greater than 30% pure possibly 90%, an amount of degradation had occurred and this is the reason for the inaccuracy in this estimate.

Insect cells apparently recognise and cleave mammalian signal sequences which direct proteins to the endoplasmic reticulum (ER). It also appears that sites which are targeted for glycosylation in insect cells (*Sp. frugiperda*) are the same as those for mammalian cells. The insect cells appear to lack galactose and sialic acid transferases and therefore cannot form 'complex' oligosaccharides, this results in trimming of the N-link to a central core of $Man_3GlcNAc_2$. Nevertheless, proteins such as interleukins and interferons made using these systems have been shown to be biologically active. TRAP produced in this manner appears to have been assembled into a dimer or trimer indicating that oligomeric forms of the polypeptide are functional.

Complementary work was carried out to explore possible variation in the DNA sequence which results in amino acid sequence. The polymerase chain reaction was again employed using oligonucleotide primers A and B. The substrate for the enzymatic reaction has been total genomic DNA from various geographical isolates. The amplified material was treated in a similar fashion prior to cloning into the Sma 1 site of the sequencing vector M13mp8 (Amersham). Using a series of nested primers it was possible to sequence the complete 1.7 kb insert for K1 (a Thai isolate different from T9/96). Some differences from the sequence of Formula I were found, as displayed in Table 1, but the conserved regions were all intact. Single base substitutions result in 22 amino acid substitutions. There is one single substitution which does not lead to an amino acid change. This maintains a cysteine residue. These sorts of results have been observed in other antigenically variable proteins involved in cell attachment screened, as well as in CS protein.

```
FORMULA 2A
Oligonucleotide sequence  ACC  ATT  TCC  ACA  GGT  TAC  ACT  ACA  TGG
                                *    *

Sequence detected         ACC  TTT  ACC  ACA  AGT  TAC  ACT  ACA  TGG

FORMULA 2B
CS protein
    Amino acid sequence    P    C    S    V    T    C    G    N    G DNA sequence          CCA  TGT  AGT  GTA  ACT  TGT  GGA  AAT  GGT TRAP
    Amino acid sequence    P    C    S    V    T    C    G    K    G DNA sequence          CCA  TGT  AGT  GTA  ACT  TGT  GGT  AAA  GGT FORMULA I
   1 taaaaatattctttgtttatattaagatatttaactttactatacacgtaattttttgtaatatatatatatat
  76 gtatattataggaagaacgtctaatatacataacattgttcttatatataatatatttgattgtgaatttatata
 151 catttatatgatatcacaccaaataaattacacttatatcaaatatacctgtgtatataaatatatgattatata
 226 atttgtatgtgcatgcgtacaagaaaatattatctttttaaggtataatatatttgttttagtattattattaaaa
                       1                                              11
                       M    N    H    L    G    N    V    K    Y    L    V    I    V    F    L    I
 301 ttgtaaaaata        ATG  AAT  CAT  CTT  GGG  AAT  GTT  AAA  TAT  TTA  GTC  ATT  GTG  TTT  TTG  ATT
                                21                                              31

F    F    D    L    F    L    V    N    G    R    D    V    Q    N    N    I    V    D    E
 360    TTC  TTT  GAT  TTG  TTT  CTA  GTT  AAT  GGT  AGA  GAT  GTG  CAA  AAC  AAT  ATA  GTG  GAT  GAA
                                     41                                         51

I    K    Y    S    E    E    V    C    N    D    Q    V    D    L    Y    L    L    M    D
 417    ATA  AAA  TAT  AGT  GAA  GAA  GTA  TGT  AAT  GAT  CAG  GTA  GAT  CTT  TAC  CTT  CTA  ATG  GAT
                                          61                                    71

C    S    G    S    I    R    R    H    N    W    V    N    H    A    V    P    L    A    M
 474    TGT  TCT  GGA  AGT  ATA  CGT  CGT  CAT  AAT  TGG  GTG  AAC  CAT  GCA  GTA  CCT  CTA  GCT  ATG
                                          81                                    91

K    L   |I    Q    Q|   L    N    L    N    D    N    A    I    H    L    Y    V    N    V
 531    AAA  TTG  ATA  CAA  CAA  TTA  AAT  CTT  AAT  GAT  AAT  GCA  AAT  CAC  TTA  TAT  GTT  AAT  GTT
                                          101                                   111

F    S    N    N    A    K    E    I    I    R    L    H    S    D    A    S    K    N    K
 588    TTT  TCA  AAC  AAT  GCA  AAA  GAA  ATT  AAT  AGA  TTA  CAT  AGT  GAT  GCA  TCT  AAA  AAC  AAA
```

```
                    E    K    A    L    I    I    I    R    S    L    L    S    T    N    L    P    Y    G    R
                                                                  121
 645 GAG AAG GCT TTA ATT ATT ATA AGG TCA CTC TTA AGT ACA AAT CTT CCA TAT GGT AGA
     131    *                                             141
         T    N    L    T    D    A    L    L    Q    V    R    K    H    L    N    D    R    I    N
 702 ACA AAC TTA ACT GAT GCA CTG TTA CAA GTA AGA AAA CAT TTA AAT GAC CGA ATC AAT
             151                                                161
         R    E    N    A    N    Q    L    V    V    I    L    T    D    G    I    P    D    S    I
 759 AGA GAG AAT GCT AAT CAA TTA GTT GTT ATA TTA ACA GAT GGA ATT CCA GAT AGT ATT
                      171                                                 181
         Q    D    S    L    K    E    S    R    K    L    S    D    R    G    V    K    I    A    V
 816 CAA GAT TCA TTA AAA GAA TCA AGA AAA TTA AGT GAT CGT GTT GTT AAA ATA GCT GTT
                           191                                                 201
         F    G    I    G    Q    G    I    N    V    A    F    N    R    F    L    V    G    C    H
 873 TTT GGT AAT GGA CAA GGT ATT AAT GTA GCT TTC AAC AGA TTT CTT GTA GGT TGT CAT
                                     211                                                 221
         P    S    D    G    K    C    N    L    Y    A    D    S    A    W    E    N    V    K    N
 930 CCA TCA GAT GGT AAA TGT AAC TTG TAT GCT GAT TCT GCA TGG GAA AAT GTA AAA AAT
                                          231                                                 241
         V    I    G    P    F    M    K    A    V    C    V    E    V    E    K    T    A    S    C
 987 GTT ATC GGA CCC TTT ATG AAG GCT GTT TGT GTT GAA GTA GAA AAA ACA GCA AGT TGT
                      247                      251                                        261
         G    V    W    D    E    W    S    P    C    S    V    T    C    G    K    G    T    R    S
1044 GGT GTT TGG GAC GAA TGG TCT CCA TGT AGT GTA ACT TGT GGT AAA GGT ACC AGG TCA
            266                           271                                                 281
         R    K    R    E    I    L    H    E    G    C    T    S    E    I    Q    E    Q    C    E
1101 AGA AAA AGA GAA ATC TTA CAC GAA GGA TGT ACA AGT GAA ATA CAA GAA CAA TGT GAA
                                               291                                           301
         E    E    R    C    P    P    K    W    E    P    L    D    V    P    D    E    P    E    D
1158 GAA GAA AGA TGT CCT CCA AAA TGG GAA CCA TTA GAT GTT CCA GAT GAA CCC GAA GAT
                                         *   311
         D    Q    P    R    P    R    G    D    N    S    S    V    Q    K    P    E    E    N    I
1215 GAT CAA CCT AGA CCA AGA GGA GAT AAT TCT TCT GTC CAA AAA CCA GAA GAA AAT ATA
     321                                                 331
         I    D    N    N    P    Q    E    P    S    P    N    P    E    E    G    K    D    E    N
1272 ATA GAT AAT AAT CCA CAA GAA CCT TCA CCA AAT CCA GAA GAA GGA AAG GAT GAA AAT
                  341                                         351
         P    N    G    F    D    L    D    E    N    P    E    N    P    P    N    P    D    I    P
1329 CCA-AAC GGA TTT GAT TTA GAT GAA AAT CCA GGA AAT CCA CCA AAT CCA GAT ATT CCT
                  361                                                   371
         E    Q    K    P    N    I    P    E    D    S    E    K    E    V    P    S    D    V    P
1386 GAA CAA AAA CCA AAT ATA CCT GAA GAT TCA GAA AAA GAA GTA CCT TCT GAT GTT CCA
                       381                                                 391
         K    N    P    E    D    D    R    E    E    N    F    D    I    P    K    K    P    E    N
1443 AAA AAT CCA GAA GAC GAT CGA GAA GAA AAC TTT GAT ATT CCA AAG AAA CCC GAA AAT
                           401                                                 411
         K    H    D    N    Q    N    N    L    P    N    D    K    S    D    R    N    I    P    Y
1500 AAG CAC GAT AAT CAA AAT AAT TTA CCA AAT GAT AAA AGT GAT AGA AAT ATT CCA TAT
                            421                                                 431
         S    P    L    P    P    K    V    L    D    N    E    R    K    Q    S    D    P    Q    S
1557 TCA CCA TTA CCT CCA AAA GTT TTG GAT AAT GAA AGG AAA CAA AGT GAC CCC CAA AGT
                            441                                                 451
         Q    D    N    N    G    N    R    H    V    P    N    S    E    D    R    E    T    R    P
1614 CAA GAT AAT AAT GGA AAT AGG CAC GTA CCT AAT AGT GAA GAT AGA GAA ACA CGT CCA
```

-continued

```
                               *   461                                  *        471
       H   G   R   N   N   E   N   R   S   Y   N   R   K   Y   N   D   T   P   K
 1671 CAT GGT AGA AAT AAT GAA AAT AGA TCA TAC AAT AGA AAA TAT AAC GAT ACT CCA AAA
                                       481                                       491
       H   P   E   R   E   E   H   E   K   P   D   N   N   K   K   K   G   E   S
 1728 CAT CCT GAA AGG GAA GAA CAT GAA AAG CCA GAT AAT AAT AAA AAA AAA GGA GAA TCA
                                           501
       D   N   K   Y   K   I   A   G   G   I   A   G   G   L   A   L   L   A   C
 1785 GAT AAT AAA TAT AAA ATT GCA GGT GGA ATA GCT GGA GGA TTA GCT TTA CTC CCA TGT
      511                                         521
       A   G   L   A   Y   K   F   V   V   P   G   A   A   T   P   Y   A   G   E
 1842 GCT GGA CTT GCT TAT AAA TTC GTA GTA CCA GGA GCA GCA ACA CCC TAT GCC GGA GAA
              531                                 541
       P   A   P   F   D   E   T   L   G   E   E   D   K   D   L   D   E   P   E
 1899 CCT GCA CCT TTT GAT GAA ACA TTA GGT GAA GAA GAT AAA GAT TTG GAC GAA CCT GAA
                  551
       Q   F   R   L   P   E   E   N   E   W   N
 1956 CAA TTC AGA TTA CCT GAA GAA AAC GAG TGG AAT taaatataatacttgaataatattttatgta
 2020 atatagtgaaatacacaacaacaaaaaaaaaaaaaaataataaaataaaataaaataaataaataaaataa
 2095 aataaaagataaaaataataaaaaaataataatagtaaggataaaaaagaataatatgaaaaatacaaatatata
 2170 tttgtatataataaaactcttataaaaattatacataatagtagcaagagaaataagattgtgttaattctttat
 2245 tttattttattttatttgtttctttttttcttttttttcttttttttcttttttttctttttttttttttttt
 2320 ttttttagtaaatcgctatatataatctattttatttactcggtaatttgttttattttttttttgaatgtgtta
 2395 ttatttgttgattacttttatgttttattctctctttaatttataatcatttatatatcactaatgaatgtgtta
 2470 ttatatataatataaattcgccatgttttttattttcttcatatatttattttgttaatttaaacattttagtaga
 2545 ataaaagaaacctataataaaaaatttcataataacaaaaattacaaaaaaaaaaaaaaaaaaaaaaaataataa
 2620 taataataataataataaatcctcatcttaacatacatatttataataatatatagaaaaaattttcctata
 2695 taaaatttaaaatgaaaaaatatatattaaactaattaagaaaaaaattaagaatacatatataaatatatataa
 2770 attatatatatatatatattaaaatatgaattacacaaattttgtgtcactaacttttagaacaaaataaata
 2845 taaaaaaaaactttacaaattgtgtctaagaaattaaattattttaattaacaaaatattgattcgaaacaaa
 2920 ttgtggaattttttaaaaaatcatcaattattttttgactcccgttttttcatcattttgttcattatccttatgatc
 2995 tttattttttaatatttaatttttcacatagaactttagaaaattcataatcgcatatttgaaaatttgtatttaa
 3070 atcttcatttataatttcattaacatcgaattc
```

FORMULAE III

```
           Residue
           nos.

TRAP       244-292  C G V W D E W S P C S V T G K G T R S R K R E I L H E G C T S E I Q E C E E R C P P K W E

CS protein
P.f.       340-388  N S I S T E W S P C S V T C G N G V R R R R K P G S A N K K P D E L D L T M D D L E K K I C T M D K
P.v.       307-355  A T V G T E W T P C S V T C G V R R R R K K P G S A A H G A E D D L T L N D D L E T D V A C V M D K
P.k.       292-340  S S V T T E W S P C S V T C G N G K R R R R K P K A H G A E D L T M D D L E T D V C T M D K
P.c.       307-355  S T I G V E E W S P C S V T C G K G V R M R K N A A A K P E D L T L E D I E I C K M D K
P.b.       269-316  D S I T E E W S P C N V T C G S G V R V R R K N K G S N K P A E D L T L E D I D T E I C K M D K
P.y.       296-342  S Q L T E E W S Q C S V T C G S G V R V R K N V N K P E N L T L E D I D T E I C K M D K Thrombospondin
           382-437  W S P W S E W T S C S T S C G N G I Q Q R R R C D S L N N P S P Q N G G K P C E G S S V Q T D S L K E F M Q K L V
           437-485  W S P W S S W S C S V T C G D G V T R R R R L C N N P T P Q M N G K P C E G E A R D V T E N Q I C K
           495-543  W G P W S P W D I C S V T C G G G V Q K R S R L C N N P T P Q F G G K D C V G D V T E N Q I C N K I W E Properdin
framework
                    W - W S P W S P C S V T C S - G - Q - R R - C - P A P - C   Q-A-C         E G   G P C A G C P
```

What is claimed is:

1. An isolated nucleic acid sequence encoding a protein comprising:

(i) the amino acid sequence of Formula I; or (ii) an amino acid sequence that has substantially the same structure and biological activity as the amino acid sequence of Formula I and comprises the sequence RGD and a sequence selected from the group consisting of WDEWSPCSVTCGKGTRSRKR,
WDEWSPCSVTCGKGTR,
EWSPCSVTCGKG,
PCSVTCGKG, and
WSPCSVTCG;

wherein antibodies specific for erythrocytic or merozoite stage proteins of the *Plasmodium falciparum* life cycle recognize said amino acid sequence of (ii);

and wherein said nucleic acid encodes a protein free of other malarial proteins.

2. An isolated nucleic acid sequence as claimed in claim 1, wherein said sequence encodes a protein which is glycosylated.

3. An isolated nucleic acid sequence as claimed in claim 1, wherein the protein has the amino acid sequence of (i).

4. An isolated nucleic acid sequence as claimed in claim 1 wherein the protein has the amino acid sequence of (ii).

5. A pharmaceutical composition comprising a nucleic acid sequence according to claim 1 and a pharmaceutically acceptable carrier.

6. An isolated nucleic acid sequence as claimed in claim 1, wherein said protein comprises the amino acid sequence of (ii) and wherein said amino acid sequence of (ii) comprises the sequence RGD and the sequence WDEWSPCSVTCGKGTRSRKR.

7. A recombinant vector containing an isolated nucleic acid sequence as claimed in claim 1.

8. A method for the preparation of a polypeptide comprising the expression of a nucleic acid sequence as claimed in claim 1 in a host/vector expression system.

9. A recombinant viral vector which is a recombinant virus containing an isolated nucleic acid sequence as claimed in claim 1.

10. A method of preparing a vector comprising the steps of:

(a) preparing a plasmid containing a nucleic acid sequence as claimed in claim 1 flanked by sequences homologous to a virus;

(b) co-transfecting a host cell with the said plasmid and genomic nucleic acid of the said virus such that homologous recombination occurs between the said plasmid and the said genomic nucleic acid to generate a recombinant viral vector containing the said nucleic acid sequence; and (c) recovering recombinant virus containing the said nucleic acid sequence.

11. An isolated nucleic acid sequence encoding a polypeptide comprising:

(i) a fragment of the amino acid sequence of Formula I of at least 20 consecutive residues; or (ii) a fragment of at least 20 consecutive residues that has substantially the same structure and biological activity as the amino acid sequence of Formula I and comprises the sequence RGD and a sequence selected from the group consisting of WDEWSPCSVTCGKGTRSRKR,
EWSPCSVTCGKG,
PCSVTCGKG, and
WSPCSVTCG;

wherein antibodies specific for erythrocytic or merozoite stage proteins of the *Plasmodium falciparum* life cycle recognize said amino acid sequence of (i) or (ii);

and wherein said nucleic acid sequence encodes a polypeptide free of other malarial proteins.

12. The nucleic acid of claim 11, wherein said fragment comprises amino acid residue 244 to amino acid residue 291 of the protein of Formula I.

13. An oligomer comprising two units, each of said units comprises a polypeptide encoded by the nucleic acid sequence claimed in claim 11.

14. An isolated nucleic acid sequence as claimed in claim 11, wherein said sequence encodes a polypeptide which is glycosylated.

15. An isolated nucleic acid sequence as claimed in claim 11, wherein the fragment of (i) comprises a sequence RGD and a sequence selected from the group consisting of:

WDEWSPCSVTCGKGTRSRKR,
WDEWSPCSVTCGKGTR,
EWSPCSVTCGKG,
PCSVTCGKG, and
WSPCSVTCG.

16. An isolated nucleic acid sequence as claimed in claim 11 wherein said fragment is the fragment of (i).

17. An isolated nucleic acid sequence as claimed in claim 11, wherein said fragment is the fragment of (ii).

18. A pharmaceutical composition comprising an isolated nucleic acid sequence according to claim 1 and a pharmaceutically acceptable carrier.

19. A nucleic acid sequence according to claim 11, wherein said polypeptide comprises the fragment of (ii) and wherein said fragment of (ii) comprises the sequence RGD and the sequence WDEWSPCSVTCGKGTRSRKR.

20. A recombinant vector containing an isolated nucleic acid sequence as claimed in claim 11.

21. A method for the preparation of a polypeptide comprising the expression of a nucleic acid sequence as claimed in claim 11 in a host/vector expression system.

22. An isolated nucleic acid sequence as claimed in claim 11, wherein said sequence encodes a polypeptide which is glycosylated.

23. The oligomer as claimed in claim 13, wherein said oligomer is glycosylated.

24. A pharmaceutical composition comprising an isolated nucleic acid sequence encoding an oligomer as claimed in claim 13 and a pharmaceutically acceptable carrier.

25. A recombinant viral vector which is a recombinant virus containing an isolated nucleic acid sequence as claimed in claim 11.

26. A method of preparing a vector comprising the steps of:

(a) preparing a plasmid containing a nucleic acid sequence as claimed in claim 11 flanked by sequences homologous to a virus;

(b) co-transfecting a host cell with the said plasmid and genomic nucleic acid of the said virus such that homologous recombination occurs between the said plasmid and the said genomic nucleic acid to generate a recombinant viral vector containing the said nucleic acid sequence; and (c) recovering recombinant virus containing the said nucleic acid sequence.

27. A vector as claimed in claim 7 which is a plasmid having a molecular length of approximately 4.38 kb, and a restriction endonuclease map as illustrated in FIG. 2.

28. A vector as claimed in claim 7 which is a plasmid having a molecular length of approximately 11.5 kb, and a restriction endonuclease map as illustrated in FIG. 3.

29. A host/vector system comprising a vector as claimed in claim 7, a host cell and wherein said host cell is capable of expressing the nucleic acid sequence.

30. A method for the preparation of a polypeptide comprising transcribing a vector as claimed in claim 7 to form a transcript and translating the transcript.

31. A vector as claimed in claim 27 which is pKR5.

32. A vector as claimed in claim 28 which is pKKJ17 the plasmid deposited on Jul., 14th 1989 at the National Collections of Industrial and Marine Bacteria Ltd. (NCIMB), Torrey Research Station, P.O. Box 31, 135 Abbey Road, Aberdeen, AB9 8DG, United Kingdom, under Accession No. NCIMB 40,164.

33. A vector as claimed in claim 9 in which the virus is a baculovirus.

34. A viral vector as claimed in claim 9 which is vKKJ17.

35. A vector as claimed in claim 33 in which the virus is *Autographa californica* Nucleopolyhedrosis Virus.

36. A vector as claimed in claim 35 in which the virus is *Autographa californica* Nucleopolyhedrosis Virus containing a plasmid having a molecular length of approximately 11.5 kb, and a restriction endonuclease map as illustrated in FIG. 3.

37. A hos/vector system comprising a vector as claimed in claim 20, a host cell and wherein said host cell is capable of expressing the nucleic acid sequence.

38. A method for the preparation of a polypeptide comprising transcribing a vector as claimed in claim 20 to form a transcript and translating the transcript.

39. A vector as claimed in claim 25 in which the virus is a baculovirus.

40. A vector as claimed in claim 39 in which the virus is *Autographa californica* Nucleopolyhedrosis Virus.

41. The virus deposited on Jul., 14th 1989 at European Collection of Animal Cell Cultures (ECACC), Public Health Service Laboratory, Centre for Applied Microbiology and Research, Porton Down, Salisbury, Wiltshire, SP4 0JG, United Kingdom, under Accession No. 89071402.

42. A host/vector system as claimed in claim 29 in which the host is selected from the species *Spodoptera frugiperda*.

43. A method for the preparation of a polypeptide which comprises expressing the nucleic acid sequence of a host/vector system as claimed in claim 29.

44. A method for the preparation of a polypeptide which comprises expressing the nucleic acid sequence of a host/vector system as claimed in claim 37.

45. A method as claimed in claim 10 in which the virus is a baculovirus.

46. A method as claimed in claim 10 in which the host cell is of the species *Spodoptera frugiperda*.

47. A method as claimed in claim 45 in which the virus is the *Autographa californica* Nucleopolyhedrosis Virus.

48. A method as claimed in claim 47 in which the recombinant virus is vKKJ17.

49. A method as claimed in claim 26 in which the virus is a baculovirus.

50. A method as claimed in claim 26 in which the host cell is of the species *Spodoptera frugiperda*.

51. A method as claimed in claim 49 in which the virus is the *Autographa californica* Nucleopolyhedrosis Virus.

\* \* \* \* \*